United States Patent

Nagamura et al.

Patent Number: 5,258,383
Date of Patent: Nov. 2, 1993

[54] DC-89 DERIVATIVES

[75] Inventors: Satoru Nagamura, Shizuoka; Hiromitsu Saito, Mishima; Eiji Kobayashi, Numazu; Katsushige Gomi, Susono, all of Japan

[73] Assignee: Kyowa Hakko Kogyo Co., Ltd., Tokyo, Japan

[21] Appl. No.: 903,756

[22] Filed: Jun. 25, 1992

[30] Foreign Application Priority Data

Jun. 28, 1991 [JP] Japan .................. 3-158896

[51] Int. Cl.⁵ ............... A61K 31/495; A61K 31/445; C07D 403/00; C07D 487/02
[52] U.S. Cl. ................... 514/253; 514/212; 514/218; 514/232.8; 514/316; 514/322; 514/410; 514/411; 540/602; 544/142; 544/373; 546/187; 546/199; 548/421; 548/433
[58] Field of Search ............... 548/421, 433; 546/199, 546/187; 544/142, 373; 540/602; 514/212, 218, 232.8, 253, 316, 322, 410, 411

[56] References Cited

U.S. PATENT DOCUMENTS

| | | | |
|---|---|---|---|
| 4,169,888 | 10/1979 | Hanaka | 548/421 |
| 4,413,132 | 11/1983 | Wierenga | 548/421 |
| 4,423,228 | 12/1983 | Wierenga | 548/421 |
| 4,423,229 | 12/1983 | Wierenga | 548/421 |
| 4,874,756 | 10/1989 | Martens et al. | 548/433 |
| 4,912,227 | 3/1990 | Kelley et al. | 548/433 |
| 4,978,757 | 12/1990 | Kelly et al. | 548/433 |
| 4,994,578 | 2/1991 | Ohba et al. | 548/433 |
| 5,070,092 | 12/1991 | Kanda et al. | 548/433 |
| 5,084,468 | 1/1992 | Saito et al. | 548/433 |
| 5,117,006 | 5/1992 | Saito et al. | 548/421 |
| 5,138,059 | 8/1992 | Takahashi et al. | 548/433 |

FOREIGN PATENT DOCUMENTS

| | | |
|---|---|---|
| 0154445 | 9/1985 | European Pat. Off. |
| 0271581 | 6/1988 | European Pat. Off. |
| 0318056 | 5/1989 | European Pat. Off. |
| 0339681 | 11/1989 | European Pat. Off. |
| 0351865 | 1/1990 | European Pat. Off. |
| 0354583 | 2/1990 | European Pat. Off. |
| 0359454 | 3/1990 | European Pat. Off. |
| 0365041 | 4/1990 | European Pat. Off. |
| 0376300 | 7/1990 | European Pat. Off. |
| 0406749 | 1/1991 | European Pat. Off. |
| 0461603 | 12/1991 | European Pat. Off. |
| 0468400 | 1/1992 | European Pat. Off. |
| 0004659 | 6/1988 | PCT Int'l Appl. |

OTHER PUBLICATIONS

Ichimura et al, CA 115-254225a (1991).
Boger et al, CA 115-84929p (1991), 115-29824a (1991).
Yasuzawa et al CA 115-28949h (1991).
Kanda et al, CA 115-8427h (1991).
Nakano et al, CA 114-41032c (1990).
Ichimura et al, CA 113-207968a (1990).
Bryson et al, CA 110-75859k (1988).

*Primary Examiner*—Cecilia Tsang
*Attorney, Agent, or Firm*—Fitzpatrick, Cella, Harper & Scinto

[57] ABSTRACT

DC-89 derivatives represented by the formula:

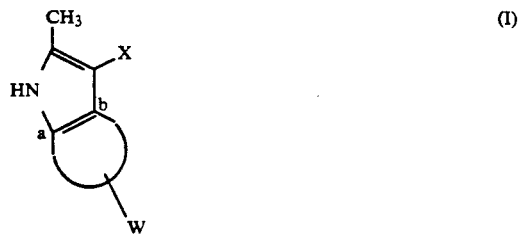

wherein X represents hydrogen or $CO_2CH_3$; and

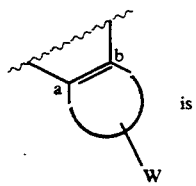

is (Abstract continued on next page.)

-continued

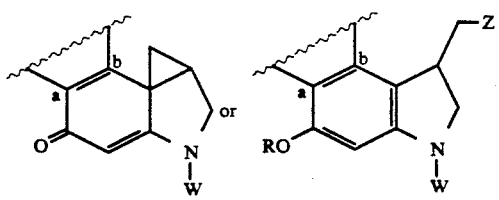

wherein Z represents Cl or Br; R represents hydrogen, CONR¹R² (in which R¹ and R² independently represent hydrogen, a straight-chain or branched alkyl group having 1 to 4 carbon atoms or phenyl) or

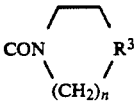

(in which n represents an integer of 0 to 4; R³ represents $CH_2$,

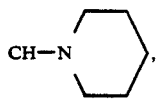

oxygen, N—$CH_3$, or N—$CH_2CONR^1R^2$ in which $R^1$ and $R^2$ have the same significances as defined above); and W represents hydrogen or

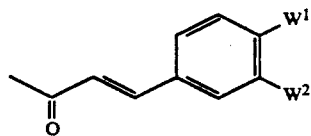

(in which $W^1$ and $W^2$ independently represent hydrogen or $OR^2$ in which $R^4$ represents a straight-chain or branched alkyl group having 1 to 4 carbon atoms or a straight-chain or branched alkenyl group having 2 to 4 carbon atoms, and pharmaceutically acceptable salts thereof have an excellent anti-tumor and antibacterial activity and are expected to be useful as anti-tumor compositions and antibacterial compositions.

8 Claims, No Drawings

DC-89 DERIVATIVES

BACKGROUND OF THE INVENTION

The present invention relates to DC-89 derivatives. The compounds exhibit an excellent anti-tumor and antibacterial activity and are expected to be useful as anti-tumor agents and antibacterial agents.

As compounds similar to the DC-89 derivatives of the present invention, DC-89A1, DC-89A2, DC-89B1 and DC-89B2 represented by the following structural formula are known. These compounds exhibit an antibacterial activity against various bacteria and also show an antitumor activity against melanoma B-16, etc.

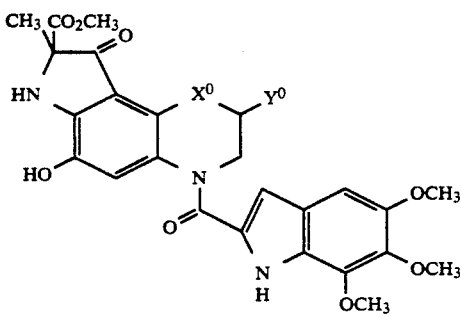

DC-89A1: $X^0$ = —CH$_2$—, $Y^0$ = Cl
DC-89A2: $X^0$ = single bond, $Y^0$ = CH$_2$Cl
DC-89B1: $X^0$ = —CH$_2$—, $Y^0$ = Br
DC-89B2: $X^0$ = single bond, $Y^0$ = CH$_2$Br DC-89A1 is disclosed in WO 87/06265 (EP-A-0271581); and DC-89A2, DC-89B1 and DC-89B2 are disclosed in Japanese Published Unexamined Patent Application No. 119787/90 (EP-A-0351865). SF2582A and SF2582B which are the same compounds as DC-89A2 and DC-89A1 respectively are disclosed in Japanese Published Unexamined Patent Application No. 139590/89 (EP-A-0318056). DC-88A and DC113 having the following structures are disclosed in WO 87/06265 and Japanese Published Unexamined Patent Application No. 177890/90 (EP-A-0376300), respectively. DC-88A and DC113 not only show an antibacterial activity against a variety of bacteria but also exhibit an anti-tumor activity against melanoma B-16, etc.

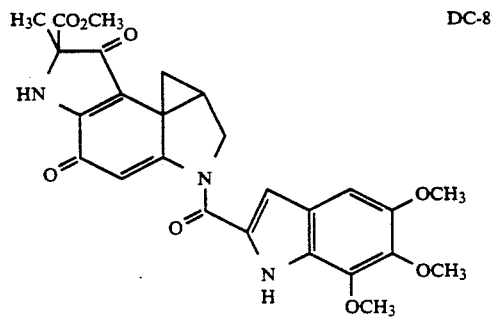

DC-88A

DC113

DC-88A derivatives and DC-89 derivatives are disclosed in Japanese Published Unexamined Patent Application No. 288879/90 (EP-A-0354583), Japanese Published Unexamined Patent Application No. 7287/91 (EP-A-0365041) and Japanese Published Unexamined Patent Application No. 128379/91 (EP-A-0406749). These derivatives are also disclosed in EP-A-0461603 and EP-A-0468400, and a patent application directed to DC-89 derivatives has been filed as Japanese Patent Application No. 21243/91.

Further, derivatives of SF2582C are disclosed in Japanese Published Unexamined Patent Application No. 275581/89 (EP-A-0339681) and CC-1065 and its derivatives are disclosed in Japanese Published Unexamined Patent Application No. 64695/79 (U.S. Pat. No. 4,169,888), Japanese Published Unexamined Patent Application No. 193989/85 (EP-A-0154445), WO 88/04659 and EP-A-0359454.

SUMMARY OF THE INVENTION

The present invention relates to DC-89 derivatives represented by formula (I):

(I)

wherein X represents hydrogen or CO$_2$CH$_3$; and is or wherein Z represents Cl or Br: R represents hydrogen, CONR¹R² (in which R¹ and R² independently represent hydrogen, a straight-chain or branched alkyl group having 1 to 4 carbon atoms or phenyl) or

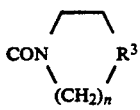

(in which n represents an integer of 0 to 4; R³ represents CH₂,

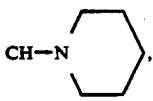

oxygen, N—CH₃, or N—CH₂CONR¹R² in which R¹ and R² have the same significances as defined above); and W represents hydrogen or

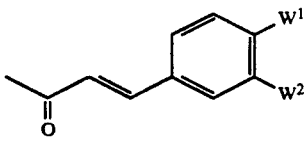

(in which W¹ and W² independently represent hydrogen or OR⁴ in which R⁴ represents a straight-chain or branched alkyl group having 1 to 4 carbon atoms or a straight-chain or branched alkenyl gropu having 2 to 4 carbon atoms), and pharmaceutically acceptable salts thereof.

DETAILED DESCRIPTION OF THE INVENTION

The compounds represented by formula (I) are hereinafter referred to as Compounds (I). Similarly, the compounds represented by formulae (II) through (IV) are referred to as Compounds (II) through (IV). Compounds (I)a, (I)b, etc. are intended to be included in Compounds (I). In the definitions of R¹ and R⁴ in formula (I), the straight-chain or branched alkyl having 1 to 4 carbon atoms include, for example, methyl, ethyl, propyl, isopropyl, butyl, isobutyl, sec-butyl and tert-butyl.

As the pharmaceutically acceptable salts of Compounds (I), inorganic acid-addition salts such as hydrochloride, hydrobromide, hydroiodide, sulfate, phosphate and nitrate, and organic acid-addition salts such as acetate, benzoate, maleate, fumarate, succinate, tartrate, citrate, oxalate, glyoxylate, aspartate and methanesulfonate may be mentioned.

The processes for preparing Compounds (I) are described below.

Process 1

Compound (I)a [Compound (I) wherein

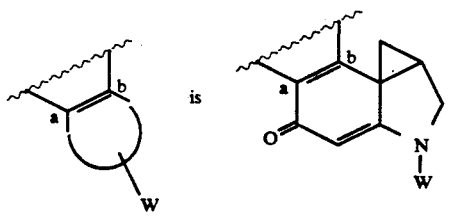

and W is hydrogen) can be prepared by treating Compound (A) shown by the formula:

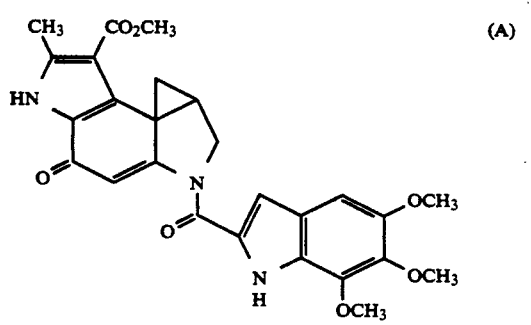

or Compound (B) shown by the formula:

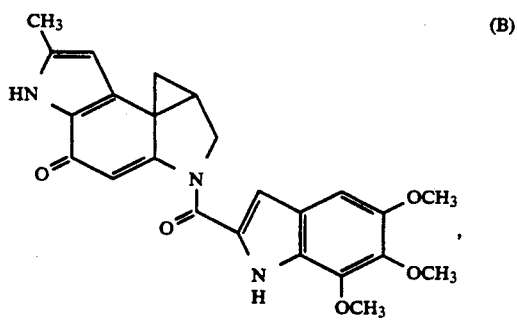

which are described in Japanese Published Unexamined Patent Application No. 128379/91 (EP-A-0406749), with a base in an inert solvent.

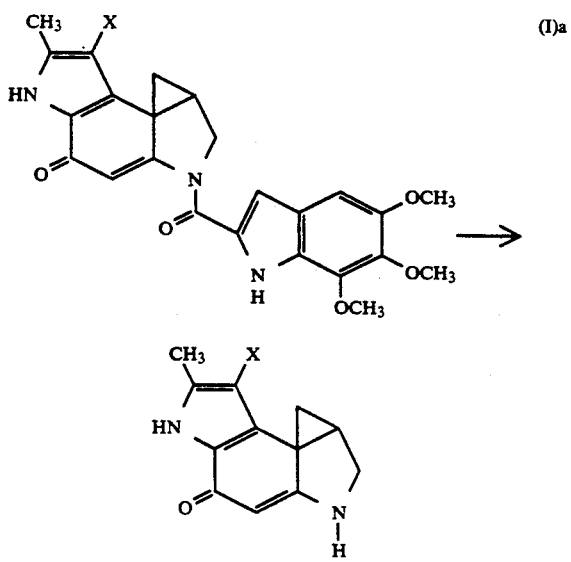

-continued

Compound (A) : X = CO₂CH₃
Compound (B) : X = H

As the base, sodium methoxide, sodium hydroxide, potassium hydroxide, potassium t-butoxide, triethylamine, 1,8-diazabicycloundecene (DBU), potassium carbonate, etc. may be used. The base is usually used in an amount of 1 to 3 equivalents based on Compound (A) or Compound (B). As the inert solvent, water, methanol, tetrahydrofuran (THF), dioxane, acetonitrile, etc. may be used singly or in combination. The reaction is generally carried out at −20° C. to 50° C. and is completed in 30 minutes to 5 hours.

Process 2

Compound (I)b [Compound (I) wherein

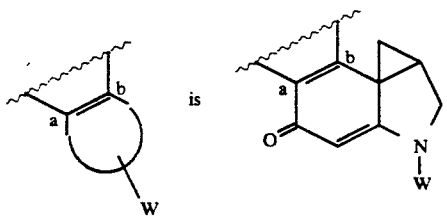

and W is a group other than hydrogen] can be prepared by allowing Compound (I)a to react with a reactive derivative of the corresponding carboxylic acid in an inert solvent in the presence of a base.

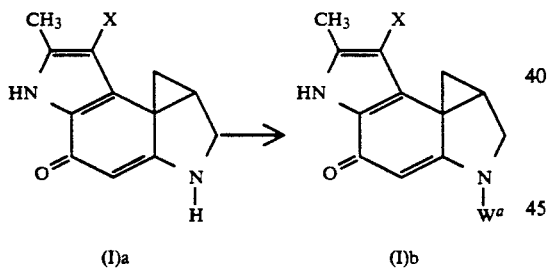

(I)a         (I)b

In these formulae, $W^a$ represents W as defined above with the exception of hydrogen and X has the same significance as defined above.

As the base, sodium hydride, lithium diisopropylamide, potassium t-butoxide, triethylamine, 4-dimethylaminopyridine, etc. may be used. The base is usually used in an amount of 1 to 2 equivalents based on Compound (I)a. As the inert solvent, dimethylformamide, THF, toluene, dimethylsulfoxide, etc. may be used singly or in combination. Examples of the reactive derivatives of carboxylic acids include acyl halides such as acid chlorides and acid bromides; activated esters such as p-nitrophenyl esters, 2,4,5-trichlorophenyl esters and N-oxysuccinimide esters, etc. The reactive derivative is usually used in an amount of 1 to 3 equivalents based on Compound (I)a. The reaction is generally carried out at −50° C. to 30° C. and is completed in 30 minutes to one day.

Process 3

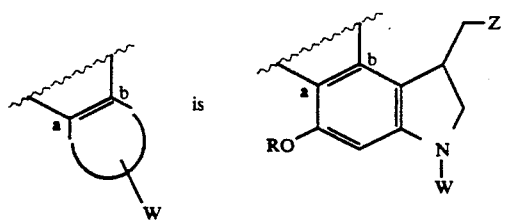

Compound (I)c [Compound (I) wherein
and R is hydrogen] can be prepared by allowing Compound (I)a or Compound (I)b to react with hydrochloric acid or hydrobromic acid in an inert solvent.

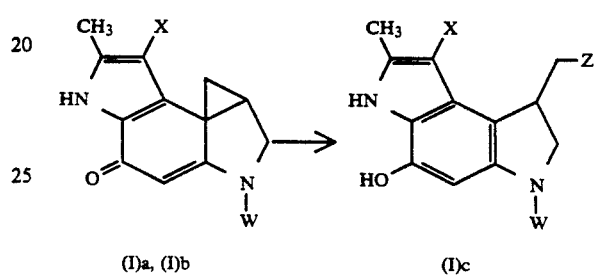

(I)a, (I)b         (I)c

In these formulae, X, W and Z have the same significances as defined above.

Hydrochloric acid or hydrobromic acid is usually used in an amount of 1 to 20 equivalents based on Compound (I)a or Compound (I)b. As the inert solvent, water, dimethylformamide, THF, toluene, dioxane, acetonitrile, etc. may be used singly or in combination. The reaction is generally carried out at −20° C. to 50° C. and is completed in 10 minutes to one hour.

Process 4-1

Compound (I)d [Compound (I) wherein

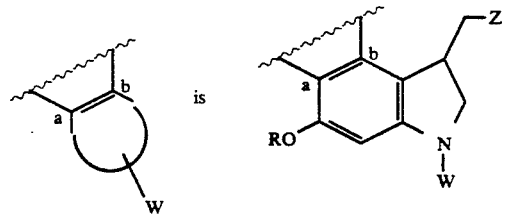

and R is $CONR^1R^2$ or

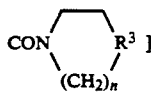

can be prepared by allowing Compound (I)c to react with Compound (II)a represented by the formula:

$R^1R^2NCOCl$      (II)a (wherein $R^1$ and $R^2$ have the same significances as defined above) or Compound (II)b represented by the formula:

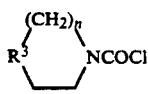

(wherein $R^3$ and n have the same significances as defined above) in an inert solvent in the presence of a base.

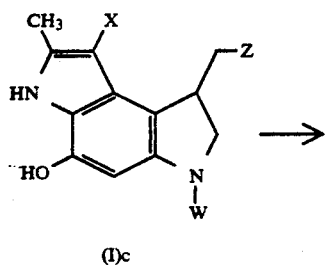

(I)c

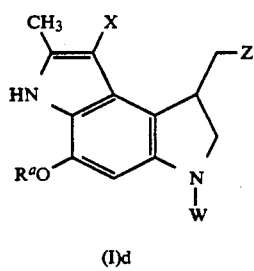

(I)d

In these formulae, $R^a$ represents $CONR^1R^2$ or

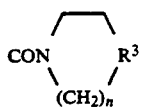

in the definition of R; and X, W and Z have the same significances as defined above.

As the base, triethylamine, pyridine, 4-dimethylaminopyridine, etc. may be used. The base is usually used in an amount of 1 to 5 equivalents based on Compound (I)c, but when the base serves also as a solvent, it may be used in large excess of Compound (I)c. As the inert solvent, pyridine, methylene chloride, dimethylformamide, THF, toluene, etc. may be used singly or in combination. Compound (II) is usually used in an amount of 1 to 10 equivalents based on Compound (I)c. The reaction is generally carried out at −50° C. to 50° C. and is completed in 30 minutes to one day.

Process 4-2

Compound (I)d can also be prepared according to the following steps.

(Step 1)

Compound (III) can be prepared by allowing Compound (I)c to react with p-nitrophenyl chloroformate in an inert solvent in the presence of a base.

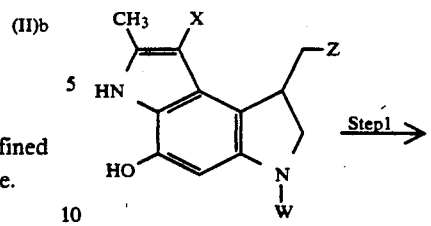

(I)c

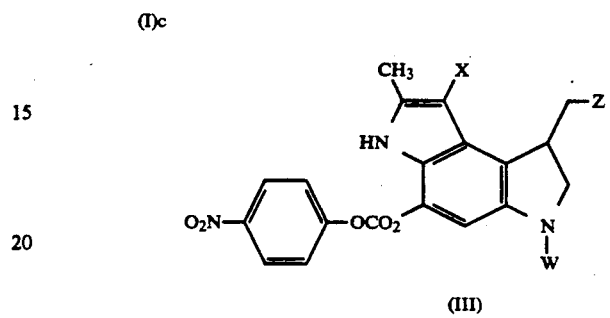

(III)

In these formulae, X, Z and W have the same significances as defined above.

p-Nitrophenyl chloroformate is usually used in an amount of 1 to 5 equivalents based on Compound (I)c. As the inert solvent, pyridine, methylene chloride, dimethylformamide, THF, toluene, etc. may be used singly or in combination. The reaction is generally carried out at −80° C. to 50° C. and is completed in 30 minutes to one day.

(Step 2)

Compound (I)d can be prepared by allowing Compound (III) to react with Compound (IV)a represented by the formula:

$R^1R^2NH$  (IV)a (wherein $R^1$ and $R^2$ have the same significances as defined above) or Compound (IV)b represented by the formula:

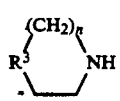

(IV)b (wherein $R^3$ and n have the same significances as defined above) in an inert solvent in the presence of a base.

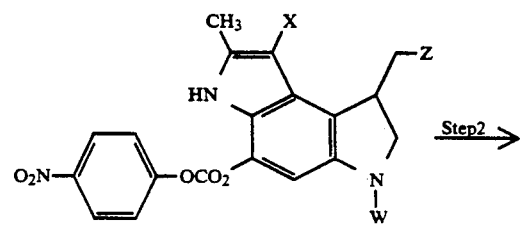

(III)

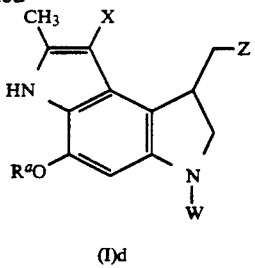

(I)d

In these formulae, $R^a$, X, Z and W have the same significances as defined above.

As the base, triethylamine, pyridine, 4-dimethylaminopyridine, etc. may be used. The base is usually used in an amount of 1 to 5 equivalents based on Compound (III), but when the base serves also as a solvent, it may be used in large excess of Compound (III). As the inert solvent, pyridine, methylene chloride, dimethylformamide, THF, toluene, etc. may be used singly or in combination. Compound (IV) is usually used in an amount of 1 to 5 equivalents based on Compound (III). The reaction is generally carried out at $-80°$ C. to $50°$ C. and is completed in 30 minutes to one day.

After completion of the reaction in each step, water, an acid or a buffer solution may be added to the reaction mixture, if necessary, followed by extraction with a water-immiscible solvent such as ethyl acetate, chloroform or ether. The extract is washed with water, an aqueous solution of sodium chloride, or the like, and dried over anhydrous sodium sulfate, or the like. Then, the solvent is distilled off, and the residue is subjected to silica gel column chromatography, thin layer chromatography, high performance liquid preparative chromatography, recrystallization, or the like to effect purification.

In the case where a salt of Compound (I) is desired and it is produced in the form of the desired salt, it can be subjected to purification as such. In the case where Compound (I) is produced in the free state and its salt is desired, Compound (I) can be converted into its salt by dissolving or suspending the compound in an appropriate solvent and adding a suitable acid to the solution or suspension.

Intermediates may be directly used in the subsequent reaction without being isolated or purified. Compounds (I) and pharmaceutically acceptable salts thereof may be in the form of adducts with water or various solvents, which are also within the scope of the present invention. Furthermore, all possible stereoisomers of Compounds (I) including optical isomers and mixtures thereof also fall within the scope of the present invention.

The structures and compound numbers of representative compounds which fall under Compounds (I) are shown in Table 1.

TABLE 1

| Compound No. | Type | X | Z | R | $W^3$ | W |
|---|---|---|---|---|---|---|
| 1 | A | $CO_2CH_3$ | — | — | — | H |
| 2 | A | $CO_2CH_3$ | — | — | $CH_3$ | MEC |
| 3 | B | $CO_2CH_3$ | Br | $CON(CH_3)_2$ | $CH_3$ | MEC |
| 4 | B | $CO_2CH_3$ | Br | CON(cyclohexyl ring) | $CH_3$ | MEC |
| 5 | B | $CO_2CH_3$ | Br | CON(pyrrolidine ring) | $CH_3$ | MEC |
| 6 | B | $CO_2CH_3$ | Br | CON(piperazine)NCH_3 | $CH_3$ | MEC |
| 7 | B | $CO_2CH_3$ | Br | CON(piperazine)NCH_3·HCl | $CH_3$ | MEC |

TABLE 1-continued

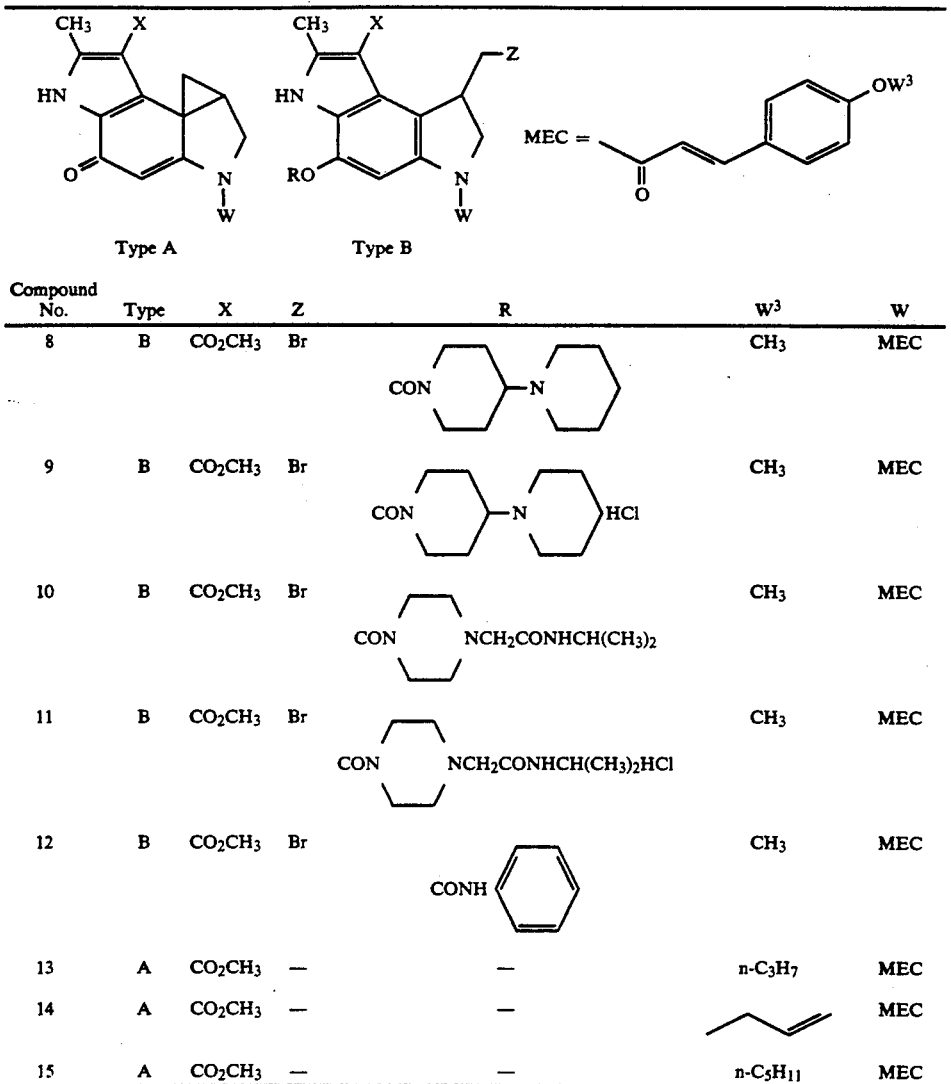

| Compound No. | Type | X | Z | R | W³ | W |
|---|---|---|---|---|---|---|
| 8 | B | $CO_2CH_3$ | Br | CON⟨piperidine⟩—N⟨piperidine⟩ | $CH_3$ | MEC |
| 9 | B | $CO_2CH_3$ | Br | CON⟨piperidine⟩—N⟨piperidine⟩HCl | $CH_3$ | MEC |
| 10 | B | $CO_2CH_3$ | Br | CON⟨piperazine⟩$NCH_2CONHCH(CH_3)_2$ | $CH_3$ | MEC |
| 11 | B | $CO_2CH_3$ | Br | CON⟨piperazine⟩$NCH_2CONHCH(CH_3)_2HCl$ | $CH_3$ | MEC |
| 12 | B | $CO_2CH_3$ | Br | CONH—phenyl | $CH_3$ | MEC |
| 13 | A | $CO_2CH_3$ | — | — | $n-C_3H_7$ | MEC |
| 14 | A | $CO_2CH_3$ | — | — | allyl | MEC |
| 15 | A | $CO_2CH_3$ | — | — | $n-C_5H_{11}$ | MEC |

The pharmacological activity of representative Compounds (I) is shown below.

Growth Inhibitory Effect against HeLaS₃ Cells

HeLaS₃ cells were suspended in a medium comprising MEM medium, 10% fetal calf serum and 2 mM glutamine (hereinafter referred to as medium A) to a concentration of $3 \times 10^4$ cells/ml. The cell suspension thus prepared was put into wells of a 96-well microtiter plate in an amount of 0.1 ml per well. After incubation at 37° C. for 20 hours in a $CO_2$ incubator, Compound (I) appropriately diluted with medium A was added to each well in an amount of 0.05 ml.

The cells were further cultured at 37° C. for 72 hours in the $CO_2$-incubator and the culture supernatant was removed. After the residue was washed once with phosphate buffer saline (PBS), a medium comprising medium A and 0.02% Neutral Red was added in an amount of 0.1 ml per well. Then, the cells were cultured at 37° C. for one hour in the $CO_2$-incubator, whereby the cells were stained. After removal of the culture supernatant, the residue was washed once with physiological saline. The pigment was extracted with 0.001N hydrochloric acid/30% ethanol and the absorbance of the extract was measured at 550 nm using a microplate reader. The concentration of the test compound at which the growth of the cells is inhibited by 50% ($IC_{50}$) was calculated by comparing the absorbance of untreated cells with those of the cells treated with the test compound at known concentrations. The result is shown in Table 2.

Therapeutic Effect against Sarcoma 180 Tumor

Five male ddY-strain mice each weighing 18 to 20 g were used for each group as test animals, and $5 \times 10^5$ Sarcoma 180 tumor cells were implanted subcutaneously into the animals at the axilla. One day after the implantation, 0.2 ml of physiological saline containing Compound (I) at the concentration indicated in Table 2 was intravenously administered to each mouse. T/C [T: average tumor volume (mm³) of the group treated with the test compound, C: average tumor volume (mm³) of the control group which received an intravenous administration of 0.2 ml of physiological saline]was determined seven days after the implant The result is shown in Table 2.

TABLE 2

| Compound No. | IC$_{50}$ (nM) | Dose (mg/kg) | T/C |
|---|---|---|---|
| 2 | 0.18 | | |
| 3 | 11 | 8.0 | 0.027 |
| 4 | <0.24 | | |
| 7 | | 4.0 | 0.20 |
| 9 | | 4.0 | 0.17 |
| 11 | | 8.0 | 0.12 |
| 12 | | 2.0 | 0.25 |

Acute Toxicity Test

A test compound was intravenously administered to ddY-strain male mice each weighing 20±1 g. MLD (the minimum lethal dose) was determined by observing the mortality for 14 days after the administration.

The result is shown in Table 3.

TABLE 3

| Compound No. | Acute Toxicity (MLD) mg/kg |
|---|---|
| 2 | 2.0 |
| 3 | >8.0 |
| 4 | >8.0 |
| 5 | >8.0 |
| 7 | 8.0 |
| 9 | 4.0 |
| 11 | >8.0 |
| 12 | 2.0 |

Compounds (I) and pharmaceutically acceptable salts thereof may be used as anti-tumor agents and antibacterial agents, singly or in combination with at least one pharmaceutically acceptable carrier. For example, Compounds (I) or salts thereof are dissolved in a physiological saline or in an aqueous solution of glucose, lactose, mannitol, or the like to prepare a pharmaceutical composition suitable for injection. Alternatively, Compounds (I) or salts thereof are freeze-dried in a conventional manner and mixed with sodium chloride to prepare a powder injection.

If necessary, the pharmaceutical composition may contain additives well known in the art of medical preparation, for example, pharmaceutically acceptable salts. Although the dose of the composition may vary depending upon the age, condition, etc. of the patient, it is suitable to administer Compound (I) in a dose of 0.01 to 20 mg/kg/day for mammals including human beings. Administration may be made, for example, once a day (single administration or consecutive administrations) or intermittently 1 to 3 times a week or once every 2 to 3 weeks, intravenously. If desired, intraarterial administration, intraperitoneal administration, intrathoracical administration, etc. are also possible in a similar dose and in a similar manner. Further, if desired, the composition may also be administered orally, in a similar dose and in a similar manner. Forms for oral administration include tablets, capsules, powders, granules and ampoules, which contain pharmaceutical auxiliaries well known in the art of medical preparation.

Certain specific embodiments of the present invention are illustrated by the following examples.

The physicochemical properties of the compounds shown in the following examples were determined with the following equipments.

| NMR | JEOL, Ltd. | FX-100 | (100 MHz) |
|---|---|---|---|
| | Bruker | AM-400 | (400 MHz) |
| | JEOL, Ltd. | GX-270 | (270 MHz) |
| | JEOL, Ltd. | EX-270 | (270 MHz) |
| MS | Hitachi Ltd. | M-80B | |
| | JEOL, Ltd. | SX-102 | |
| IR | Japan Spectral Co., Ltd. | | IR-810 |

As the silica gel, Wakogel C-200 ® manufactured by Wako Pure Chemical Industries, Ltd. was used.

EXAMPLE 1

Synthesis of Compound 1

In 2 ml of methanol was dissolved 14 mg [0.029 mmol] of Compound (A), and 0.03 ml of methanol containing 28 wt% sodium methoxide (0.16 mmol) was added to the solution. The mixture was stirred at room temperature for one hour. To the reaction mixture was added 0.2 M phosphate buffer of pH 7, followed by extraction with chloroform. The chloroform layer was washed with a saturated aqueous solution of sodium chloride, dried over anhydrous sodium sulfate, and then concentrated under reduced pressure. The resulting crude product was purified by silica gel column chromatography (20 ml of silica gel, chloroform : methanol =25 : 1) to give 7.4 mg (yield 99%) of Compound 1.

The physicochemical properties of Compound 1 are as follows.

$^1$H-NMR (400MHz, CDCl$_3$+DMSO-d$_6$) δ(ppm); 11.72(1H, br s), 6.92(1H, br s), 5.34(1H, s), 3.72(3H, s), 3.67(1H, dd, J=10.6, 5.3Hz), 3.51(1H, dd, J=10.6, 10.6Hz), 3.39(1H, m), 2.46(3H, s), 1.98(1H, dd, J=7.7, 2.4Hz), 0.98(1H, dd, J=4.6, 2.9Hz), SIMS (m/z); 259(M+H)+

IR (KBr) ν(cm$^{-1}$); 1682, 1607, 1573, 1458, 1379, 1305, 1273, 1229, 1194, 1156, 1108

EXAMPLE 2

Synthesis of Compound 2

To 2 ml of N,N-dimethylformamide was added 23 mg (0.57 mmol) of 60% sodium hydride, and 2 ml of N,N-dimethylformamide containing 95.6 mg (0.37 mmol) of Compound 1 obtained in Example 1 was added to the mixture, followed by stirring at 0° C. for two hours in an argon atmosphere. The reaction mixture was cooled to −50° C. and 2 ml of N,N-dimethylformamide containing 166 mg [0.56 mmol] of 4-nitrophenyl 4-methoxycinnamate was added thereto. The mixture was stirred at −50° C. to room temperature for one hour. After 0.2M phosphate buffer of pH 7 was added to the reaction mixture, extraction was carried out with ethyl acetate. The ethyl acetate layer was washed with a saturated aqueous solution of sodium chloride, dried over anhydrous sodium sulfate, and then concentrated under reduced pressure. The resulting crude product was purified by silica gel column chromatography (20 ml of silica gel, chloroform : methanol =50 : 1) to give 132 mg (yield 85%) of Compound 2.

The physicochemical properties of Compound 2 are as follows.

$^1$H-NMR (400MHz, CDCl$_3$) δ(ppm); 11.14(1H, br), 7.79 (1H, d, J=15.4Hz), 7.52(2H, d, J=8.7Hz), 7.26 (1H, s), 6.91(2H, d, J=8.8Hz), 6.75(1H, d, J=15.4Hz), 4.24(1H, dd, J=10.9, 10.9Hz), 4.15(1H, dd, J=10.9, 4.8Hz), 3.85(3H, s), 3.82(3H, s), 3.56(1H, m), 2.62(3H, s), 2.39(1H, dd, J=7.6, 3.5Hz), 1.31(1H, dd, J=4.9, 3.5Hz)

EIMS (m/z); 419(M)+

IR (KBr) $\nu(cm^{-1})$; 1702, 1601, 1512, 1390, 1292, 1241, 1225, 1173, 1110, 1072

EXAMPLE 3

Synthesis of Compound 3

In 3 ml of acetonitrile was dissolved 30 mg (0.072 mmol) of Compound 2 obtained in Example 2, and 1.5 ml of 48% hydrobromic acid was added to the solution. The mixture was stirred at room temperature for one hour. To the reaction mixture was added 1N hydrobromic acid, followed by extraction with chloroform. The chloroform layer was dried over anhydrous sodium sulfate, and then concentrated under reduced pressure. The resulting crude product was dissolved in 3 ml of methylene chloride, and 3 ml of methylene chloride containing 36 mg (0.179 mmol) of p-nitrophenyl chloroformate was added to the solution at −78° C. Then, 0.025 ml (0.180 mmol) of triethylamine was added to the mixture, followed by stirring for 0.5 hour. After 0.032 ml (0.356 mmol) of a 50% aqueous solution of dimethylamine was added to the reaction mixture, the mixture was stirred at −78° C. to room temperature for 0.5 hour. Then, 0.2M phosphate buffer of pH 7 was added to the reaction mixture, followed by extraction with chloroform. The chloroform layer was washed with a saturated aqueous solution of sodium chloride, dried over anhydrous sodium sulfate, and then concentrated under reduced pressure. The resulting crude product was purified by silica gel column chromatography (30 ml of silica gel, chloroform : methanol =100 : 1) to give 36 mg (yield 90%) of Compound 3.

The physicochemical properties of Compound 3 are as follows.

$^1$H-NMR (400MHz, CDCl$_3$) δ(ppm); 8.98(1H, br), 8.25(1H, s), 7.80(1H, d, J=15.5Hz), 7.56(2H, d, J=8.7Hz), 6.93(2H, d, J=8.8Hz), 6.81(1H, d, J=15.5Hz), 4.56 (1H, m), 4.48(1H, br d, J=10.6Hz), 4.30(1H, dd, J=9.1, 2.4Hz), 3.94(3H, s), 3.86(3H, s), 3.81(1H, dd, J=10.4, 1.7Hz), 3.34(1H, dd, J=10.5, 10.4Hz), 3.18(3H, s), 3.06(3H, s), 2.60(3H, s)

SIMS (m/z); 572, 570(M+H)$^{30}$

IR (KBr) $\nu(cm^{-1})$; 2364, 1701, 1686, 1637, 1601, 1511, 1399, 1250, 1173, 1109, 1091

EXAMPLE 4

Synthesis of Compound 4

In 5 ml of acetonitrile was dissolved 20 mg (0.048 mmol) of Compound 2 obtained in Example 2, and 2.2 ml of 1N hydrobromic acid was added to the solution. The mixture was stirred at room temperature for one hour. To the reaction mixture was added 1N hydrobromic acid, followed by extraction with chloroform. The chloroform layer was dried over anhydrous sodium sulfate, and then concentrated under reduced pressure. The resulting crude product was dissolved in 3 ml of methylene chloride, and 19.3 mg [0.096 mmol) of p-nitrophenyl chloroformate was added to the solution at −10° C. Then, 0.013 ml (0.096 mmol) of triethylamine was added to the mixture, followed by stirring for 0.5 hour. After 0.014 ml (0.14 mmol) of piperidine was added to the reaction mixture, the mixture was stirred at -10° C to room temperature for 0.5 hour. Then, 0.2 M phosphate buffer of pH 7 was added to the reaction mixture, followed by extraction with chloroform. The chloroform layer was washed with a saturated aqueous solution of sodium chloride, dried over anhydrous sodium sulfate, and then concentrated under reduced pressure. The resulting crude product was purified by silica gel column chromatography [30 ml of silica gel, n-hexane ethyl acetate =1 : 1) to give 22 mg (yield 75%) of Compound 4.

The physicochemical properties of Compound 4 are as follows.

$^1$H-NMR (400MHz, CDCl$_3$) δ(ppm); 9.21(1H, br), 8.22(1H, s), 7.80(1H, d, J=15.2Hz), 7.57(2H, d, J=8.7Hz), 6.94(2H, d, J=8.8Hz), 6.81(1H, d, J=15.1Hz), 4.54 (1H, m), 4.47(1H, br d, J=10.5Hz), 4.31(1H, dd, J=9.2, 9.2Hz), 3.95(3H, s), 3.86(3H, s), 3.80(1H, dd, J=10.2, 2.2Hz), 3.68(2H, br), 3.55(2H, br), 3.21(1H, dd, J=10.2, 10.2Hz), 2.53(3H, s), 1.68 (6H, br)

SIMS (m/z); 612, 610(M+H)$^+$

IR (KBr) $\nu(cm^{-1})$; 2930, 2364, 1694, 1649, 1599, 1511, 1431, 1408, 1244, 1215, 1092, 1025

EXAMPLE 5

Synthesis of Compound 5

In 5 ml of acetonitrile was dissolved 20 mg (0.048 mmol) of Compound 2 obtained in Example 2, and 2.2 ml of 1 N hydrobromic acid was added to the solution. The mixture was stirred at room temperature for one hour. To the reaction mixture was added 1 N hydrobromic acid, followed by extraction with chloroform. The chloroform layer was dried over anhydrous sodium sulfate, and then concentrated under reduced pressure. The resulting crude product was dissolved in 3 ml of methylene chloride, and 19.3 mg (0.096 mmol) of p-nitrophenyl chloroformate was added to the solution at −10° C. Then, 0.013 ml (0.096 mmol) of triethylamine was added to the mixture, followed by stirring for 0.5 hour. After 0.012 ml (0.14 mmol) of pyrrolidine was added to the reaction mixture, the mixture was stirred at −10° C. to room temperature for 0.5 hour. Then, 0.2M phosphate buffer of pH 7 was added to the reaction mixture, followed by extraction with chloroform. The chloroform layer was washed with a saturated aqueous solution of sodium chloride, dried over anhydrous sodium sulfate, and then concentrated under reduced pressure. The resulting crude product was purified by silica gel column chromatography (30 ml of silica gel, chloroform : methanol =100 : 1) to give 22 mg (yield 76%) of Compound 5.

The physicochemical properties of Compound 5 are as follows.

$^1$H-NMR (400MHz, CDCl$_3$) δ(ppm); 8.92(1H, br), 8.26(1H, s), 7.80(1H, d, J=15.2Hz), 7.57(2H, d, J=8.7Hz), 6.94(2H, d, J=8.8Hz), 6.80(1H, d, J=15.1Hz), 4.57(1H, m), 4.47(1H, br d, J=10.3Hz), 4.30(1H, dd, J=9.0, 9.0Hz), 3.96(3H, s), 3.86(3H, s), 3.81 (1H, dd, J=10.2, 2.1Hz), 3.65(2H, t, J=6.6Hz), 3.51(2H, t, J=6.6Hz), 3.22(1H, dd, J=10.2, 10.2 Hz), 2.69(3H, s), 2.00(4H, br)

SIMS (m/z); 598, 596(M+H)$^+$

IR (KBr) $\nu(cm^{-1})$; 2944, 1697, 1637, 1491, 1412, 1313, 1218, 1109, 1087

EXAMPLE 6

Synthesis of Compound 6

In 5 ml of acetonitrile was dissolved 50 mg [0.12 mmol) of Compound 2 obtained in Example 2, and 2.5 ml of 48% hydrobromic acid was added to the solution. The mixture was stirred at room temperature for one hour. To the reaction mixture was added 1 N hydrobromic acid, followed by extraction with chloroform. The chloroform layer was dried over anhydrous sodium sulfate, and then concentrated under reduced pressure. The resulting crude product was dissolved in 5 ml of methylene chloride, and ml of methylene chloride containing 61 mg (0.30 mmol) of p-nitrophenyl chloroformate was added to the solution at −78° C. Then, 0.042 ml (0.30 mmol) of triethylamine was added to the mixture, followed by stirring for 0.5 hour. After 0.040 ml (0.36 mmol) of N-methylpiperazine was added to the reaction mixture, the mixture was stirred at −78° C. to room temperature for 0.5 hour. Then, 0.2M phosphate buffer of pH 7 was added to the reaction mixture, followed by extraction with chloroform. The chloroform layer was washed with a saturated aqueous solution of sodium chloride, dried over anhydrous sodium sulfate, and then concentrated under reduced pressure. The resulting crude product was purified by silica gel column chromatography (30 ml of silica gel, chloroform : methanol =20 : 1) to give 67 mg (yield 89%) of Compound 6.

The physicochemical properties of Compound 6 are as follows.

huH-NMR (400MHz, CDCl$_3$) δ(ppm); 9.79(1H, br), 8.21(1H, s), 7.77(1H, d, J=15.2Hz), 7.57(2H, d, J=8.8Hz), 6.93(2H, d, J=8.8Hz), 6.78(1H, d, J=15.3Hz), 4.53(1H, m), 4.41(1H, br d, J=10.5Hz), 4.25(1H, dd, J=9.3, 9.3Hz), 3.95(2H, br), 3.93(3H, s), 3.86(3H, s), 3.84(2H, br), 3.79(1H, dd, J=9.7, 2.6Hz), 3.22(1H, dd, J=10.2, 10.2Hz), 2.94(4H, br), 2.67(3H, s), 2.62(3H, s)

SIMS (m/z); 627, 625(M+H)+

IR (KBr) ν(cm$^{-1}$); 2360, 1692, 1647, 1602, 1507, 1400, 1291, 1217, 1173, 1094

EXAMPLE 7

Synthesis of Compound 7

In a mixture of 2 ml of ethanol and 4 ml of methanol was dissolved 45 mg (0.072 mmol) of Compound 6 obtained in Example 6, and 0.025 ml of 5.8 N hydrogen chloride-ethanol was added to the solution, followed by stirring at 0° C. for one hour. The reaction mixture was concentrated under reduced pressure to give 47 mg (yield of Compound 7.

The physicochemical properties of Compound 7 are as follows.

$^1$H-NMR (400MHz, DMSO-d$_6$) δ(ppm); 12.07(1H, br), 10.57 (1H, br), 8.10(1H, s), 7.74(2H, d, J=8.8Hz), 7.58(1H, d, J=15.3Hz), 7.06(1H, d, J=15.3Hz), 7.00(2H, d, J=8.8Hz), 4.50(1H, m), 4.42(3H, br), 4.17(1H, br), 3.85(3H, s), 3.82(3H, s), 3.79(1H, br), 3.58(3H, br), 3.50(4H, br), 2.86(3H, s), 2.68(3H, s)

IR (KBr) ν(cm$^{-1}$); 2364, 1740, 1705, 1648, 1599, 1511, 1405, 1251, 1218, 1173, 1095, 1023

EXAMPLE 8

Synthesis of Compound 8

In 1.5 ml of acetonitrile was dissolved 25 mg (0.06 mmol) of Compound 2 obtained in Example 2, and 1.5 ml of 48% hydrobromic acid was added to the solution. The mixture was stirred at room temperature for one hour. To the reaction mixture was added 1N hydrobromic acid, followed by extraction with chloroform. The chloroform layer was dried over anhydrous sodium sulfate, and then concentrated under reduced pressure. The resulting crude product was dissolved in 2 ml of dichloromethane, and 37 mg (0.18 mmol) of p-nitrophenyl chloroformate was added to the solution at −78° C. Then, 0.025 ml (0.18 mmol) of triethylamine was added to the mixture, followed by stirring for 0.5 hour. After 35 mg (0.21 mmol) of piperidinopiperidine was added to the reaction mixture, the mixture was stirred at −78° C. to 0° C. for 0.5 hour. Then, 0.2M phosphate buffer of pH 7 was added to the reaction mixture, followed by extraction with chloroform. The chloroform layer was washed with a saturated aqueous solution of sodium chloride, dried over anhydrous sodium sulfate, and then concentrated under reduced pressure. The resulting crude product was purified by silica gel column chromatography (20 ml of silica gel, chloroform : methanol =10 : 1) to give 38 mg (yield 91%) of Compound 8.

The physicochemical properties of Compound 8 are as follows:

$^1$H-NMR (270MHz, CDCl$_3$) δ(ppm); 9.14(1H, br), 8.23(1H, s), 7.79(1H, d, J=15.2Hz), 7.58(2H, d, J=8.6Hz), 6.94(2H, d, J=8.6Hz), 6.80(1H, d, J=15.2Hz), 4.57 (1H, m), 4.45(2H, m), 4.33(2H, m), 3.96(3H, s), 3.86(3H, s), 3.79(1H, br d, J=9.7Hz), 3.22(1H, dd, J=10.0, 10.0Hz), 3.03(1H, m), 2.88(1H, m), 2.66(3H, s), 2.62(5H, br), 1.92(2H, br), 1.67(6H, br), 1.49(2H, br)

FABMS (m/z); 695, 693(M+H)+

IR (KBr) ν(cm$^{-1}$); 1701, 1642, 1599, 1560, 1542, 1515, 1409, 1253, 1208, 1092

EXAMPLE 9

Synthesis of Compound 9

In a mixture of 1 ml of ethanol and 0.5 ml of methanol was dissolved 26 mg (0.037 mmol) of Compound 8 obtained in Example 8, and 0.008 ml of 6.86 N hydrogen chloride-ethanol was added to the solution, followed by stirring at room temperature for one hour. The reaction mixture was concentrated under reduced pressure to give mg (yield 96%) of Compound 9.

The physicochemical properties of Compound 9 are as follows:

$^1$H-NMR (270MHz, DMSO-d$_6$) δ(ppm); 12.02(1H, s), 9.96 (1H, br), 8.05(1H, s), 7.74(2H, d, J=8.9Hz), 7.57(1H, d, J=15.3Hz), 7.05(1H, d, J=15.4Hz), 6.99(1H, d, J=8.9Hz), 4.46(2H, m), 4.41(2H, br), 4.19(1H, br d, J=13.3Hz), 3.84(3H, s), 3.80(3H, s), 3.77(1H, br), 3.47(5H, br), 3.13(1H, br d, J=12.9Hz), 2.95(2H, br), 2.66(3H, s), 2.15(2H, br), 1.82(6H, br), 1.70(2H, br)

IR(KRr) ν(cm$^{-1}$); 1688, 1646, 1598, 1514, 1407, 1252, 1213, 1093, 1023

EXAMPLE 10

Synthesis of Compound 10

In 1.5 ml of acetonitrile was dissolved 25 mg (0.06 mmol) of Compound 2 obtained in Example 2, and 1.5 ml of 48% hydrobromic acid was added to the solution. The mixture was stirred at room temperature for one hour. To the reaction mixture was added 1N hydrobromic acid, followed by extraction with chloroform. The chloroform layer was dried over anhydrous sodium sulfate, and then concentrated under reduced pressure. The resulting crude product was dissolved in 2 ml of dichloromethane, and 37 mg (0.18 mmol) of p-nitrophenyl chloroformate was added to the solution at −78° C. Then, 0.025 ml (0.18 mmol) of triethylamine was added to the mixture, followed by stirring for 0.5 hour. After 39 mg (0.21 mmol) of N-isopropyl-1-piperazineacetamide was added to the reaction mixture, the mixture was stirred at −78° C. to 0° C. for 0.5 hour. Then, 0.2M phosphate buffer of pH 7 was added to the reaction mixture, followed by extraction with chloroform. The chloroform layer was washed with a saturated aqueous solution of sodium chloride, dried over anhydrous sodium sulfate, and then concentrated under reduced pressure. The resulting crude product was purified by silica gel column chromatography (20 ml of silica gel, chloroform : methanol =20 : 1) to give 31 mg (yield 73%) of Compound 10.

The physicochemical properties of Compound 10 are as follows.

$^1$H-NMR (270MHz, CDCl$_3$) δ(ppm); 8.96(1H, br s), 8.25 (1H, s), 7.80(1H, d, J=15.5Hz), 7.57(2H, d, J=8.5Hz), 6.94(2H, d, J=8.5Hz), 6.80(1H, d, J=15.5Hz), 6.80(1H, m), 4.58(1H, m), 4.47(1H, br d, J=10.9Hz), 4.31(1H, dd, J=8.9, 8.9Hz), 3.96(3H, s), 3.86(3H, s), 3.79(2H, m), 3.63(2H, br), 3.23 (1H, dd, J=10.0, 10.0Hz), 3.05(2H, s), 2.67(3H, s), 2.61(4H, br), 1.27(1H, m), 1.19(6H, d, J=6.3Hz)

FABMS (m/z); 712, 710(M+H)+

IR (KBr) ν[cm$^{-1}$]; 1701, 1646, 1602, 1561, 1514, 1409, 1305, 1249, 1219, 1189, 1093

EXAMPLE 11

Synthesis of Compound 11

In a mixture of 1 ml of ethanol and 1 ml of methanol was dissolved 18 mg (0.025 mmol) of Compound 10 obtained in Example 10, and 0.006 ml of 6.86 N hydrogen chloride-ethanol was added to the solution, followed by stirring at room temperature for three hours. The reaction mixture was concentrated under reduced pressure to give 18 mg (yield 96%) of Compound 11.

The physicochemical properties of Compound 11 are as follows.

$^1$H-NMR (270MHz, DMSO-d$_6$) δ(ppm); 12.21(1H, s), 10.39 (1H, br), 8.60(1H, br s), 8.09(1H, s), 7.75(2H, d, J=8.4Hz), 7.57(1H, d, J=14.3Hz), 7.06(1H, d, J=14.3Hz), 6.99(1H, d, J=8.4Hz), 4.41(3H, m), 4.12(1H, m), 3.91(4H, m), 3.84(3H, s), 3.81(3H, s), 3.77(1H, m), 3.69(6H, m), 2.68(3H, s), 1.22 (1H, m), 1.11(6H, d, J=6.4Hz)

IR (KBr) ν(cm$^{-1}$); 1678, 1643, 1599, 1515, 1409, 1251, 1212, 1095, 1032

EXAMPLE 12

Synthesis of Compound 12

In 1.5 ml of acetonitrile was dissolved 25 mg (0.06 mmol) of Compound 2 obtained in Example 2, and 1.5 ml of 48% hydrobromic acid was added to the solution. The mixture was stirred at room temperature for one hour. To the reaction mixture was added 1N hydrobromic acid, followed by extraction with chloroform. The chloroform layer was dried over anhydrous sodium sulfate, and then concentrated under reduced pressure. The resulting crude product was dissolved in 2 ml of dichloromethane. To the solution were added 0.033 ml (0.30 mmol) of phenyl isocyanate and 0.042 ml (0.30 mmol) of triethylamine at 0° C., and the mixture was subjected to reaction at 0° C. for three hours. Then, 0.2 M acetate buffer of pH 4 was added to the reaction mixture, followed by extraction with chloroform. The chloroform layer was washed with a saturated aqueous solution of sodium chloride, dried over anhydrous sodium sulfate, and then concentrated under reduced pressure. The resulting crude product was purified by silica gel column chromatography (20 ml of silica gel, chloroform : methanol =30 : 1) to give 18 mg (yield 48%) of Compound 12.

The physicochemical properties of Compound 12 are as follows.

$^1$H-NMR (270MHz, CDCl$_3$) δ(ppm); 9.69(1H, s), 8.35(1H, s), 7.78(1H, d, J=15.5Hz), 7.71(1H, br s), 7.53 (2H, d, J=8.9Hz), 7.29-6.99(5H, m), 6.91(2H, d, J=8.8Hz), 6.75(1H, d, J=15.6Hz), 4.44(1H, m), 4.35(1H, br d, J=11.2Hz), 4.14(1H, dd, J=10.2, 8.9Hz), 3.91(3H, s), 3.85(3H, s), 3.69(1H, br d, J=10.2Hz), 3.09(1H, dd, J=9.8, 9.8Hz), 2.52(3H, s)

FABMS (m/z); 620, 618(M+H)+

IR (KBr) ν[cm$^{-1}$]; 1733, 1699, 1642, 1603, 1514, 1444, 1412, 1305, 1253, 1204, 1092

EXAMPLE 13

Synthesis of Compound 13

In 0.1 ml of N,N-dimethylformamide was dissolved 3 mg (0.075 mmol) of 60% sodium hydride, and 0.3 ml of N,Ndimethylformamide containing 16 mg (0.062 mmol) of Compound 1 obtained in Example 1 was added to the solution. The mixture was stirred at −20° C. for three hours in an argon atmosphere. To the reaction mixture was added 0.5 ml of N,N-dimethylformamide containing 25 mg (0.076 mmol) of 4-nitrophenyl 4-propyloxycinnamate, followed by stirring at −20° C. to 0° C. for one hour. After 0.2M phosphate buffer of pH 7 was added to the reaction mixture, extraction was carried out with ethyl acetate. The ethyl acetate layer was washed with a saturated aqueous solution of sodium chloride, dried over anhydrous sodium sulfate, and then concentrated under reduced pressure. The resulting crude product was purified by silica gel column chromatography (20 ml of silica gel, chloroform : methanol =100 : 1) to give 22 mg (yield 80%) of Compound 13.

The physicochemical properties of Compound 13 are as follows.

$^1$H-NMR (400MHz, CDCl$_3$) δ(ppm); 10.01(1H, br), 7.77 (1H, d, J=15.4Hz), 7.32-6.93(4H, m), 6.84(1H, d, J=15.7Hz), 6.67(1H, br), 4.24(1H, dd, J=11.0,1 11.0Hz), 4.15(1H, dd, J=11.0, 4.7Hz), 3.94(2H, t, J=6.3Hz), 3.82(3H, s), 3.55(1H, m), 2.59(3H, s), 2.39(1H, dd, J=7.5, 3.2Hz), 1.82(2H, m), 1.31 (1H, dd, J=4.9, 3.7Hz), 1.05(3H, t, J=7.4Hz)

SIMS (m/z); 447(M+H)+, 259

IR (KBr) ν(cm$^{-1}$); 1697, 1654, 1596, 1437, 1388, 1292, 1246, 1213, 1110

EXAMPLE 14

Synthesis of Compound 14

In 0.1 ml of N,N-dimethylformamide was dissolved 3 mg (0.075 mmol) of 60% sodium hydride, and 0.3 ml of N,N-dimethylformamide containing 16 mg (0.062 mmol) of Compound 1 obtained in Example 1 was added to the solution. The mixture was stirred at −20° C. for three hours in an argon atmosphere. To the reaction mixture was added 0.5 ml of N,N-dimethylformamide containing 25 mg (0.077 mmol) of 4-nitrophenyl 4-propenyloxycinnamate, followed by stirring at −20° C. to 0° C. for one hour. After 0.2M phosphate buffer of pH 7 was added to the reaction mixture, extraction was carried out with ethyl acetate. The ethyl acetate layer was washed with a saturated aqueous solution of sodium chloride, dried over anhydrous sodium sulfate, and then concentrated under reduced pressure. The resulting crude product was purified by silica gel column chromatography (20 ml of silica gel, chloroform : methanol =100 : 1) to give 24 mg (yield 87%) of Compound 14.

The physicochemical properties of Compound 14 are as follows.

$^1$H-NMR (400MHz, CDCl$_3$) δ(ppm); 10.51(1H, br), 7.77 (1H, d, J=15.6Hz), 7.33-6.95(4H, m), 6.84(1H, d, J=15.6Hz), 6.77(1H, br), 6.07(1H, m), 5.43(1H, dd, J=17.4, 1.8Hz), 5.31(1H, dd, J=10.5, 1.2Hz), 4.57(2H, dt, J=5.1, 1.5Hz), 4.25(1H, dd, J=10.9, 10.9Hz), 4.15(1H, dd, J=11.0, 4.6Hz), 3.82(3H, s), 3.57(1H, m), 2.60(3H, s), 2.40(1H, dd, J=7.6, 3.5Hz), 1.32(1H, dd, J=4.7, 3.7Hz)

SIMS (m/z); 445(M+H)$^+$, 259

IR (KBr) ν(cm$^{-1}$); 1701, 1603, 1486, 1445, 1388, 1292, 1246, 1215, 1109

EXAMPLE 15

Synthesis of Compound 15

In 0.1 ml of N,N-dimethylformamide was dissolved 3 mg (0.075 mmol) of 60% sodium hydride, and 0.3 ml of N,N-dimethylformamide containing 16 mg (0.062 mmol) of Compound 1 obtained in Example 1 was added to the solution. The mixture was stirred at −20° C. for three hours in an argon atmosphere. To the reaction mixture was added 0.5 ml of N,N-dimethylformamide containing 27 mg (0.076 mmol) of 4-nitrophenyl 4-pentyloxycinnamate, followed by stirring at −20° C. to 0° C. for one hour. After 0.2M phosphate buffer of pH 7 was added to the reaction mixture, extraction was carried out with ethyl acetate. The ethyl acetate layer was washed with a saturated aqueous solution of sodium chloride, dried over anhydrous sodium sulfate, and then concentrated under reduced pressure. The resulting crude product was purified by silica gel column chromatography (20 ml of silica gel, chloroform : methanol =100 : 1) to give 24 mg (yield 82%) of Compound 15. The physicochemical properties of Compound 15 are as follows.

$^1$H-NMR (400MHz, CDCl$_3$) δ(ppm); 10.34(1H, br), 7.78 (1H, d, J=15.4Hz), 7.52-6.93(4H, m), 6.85(1H, d, J=15.4Hz), 6.67(1H, br), 4.24(1H, dd, J=11.0, 1.0Hz), 4.15(1H, dd, J=11.0, 4.6Hz), 3.99(2H, t, J=6.6Hz), 3.82(3H, s), 3.55(1H, m), 2.61(3H, s), 2.39(1H, dd, J=7.6, 3.4Hz), 1.81(2H, m), 1.44(4H, m), 1.31(1H, dd, J=4.9, 3.7Hz), 0.94(3H, t, J=7.0Hz)

SIMS (m/z); 475(M+H)$^+$, 259

IR (KBr) ν(cm$^{-1}$); 1701, 1628, 1599, 1457, 1389, 1255, 216, 1109

What is claimed is:

1. A DC-89 derivative represented by the formula:

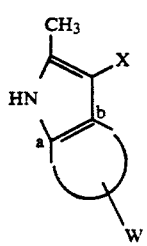

(I)

wherein X represents hydrogen or CO$_2$CH$_3$; and

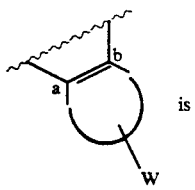

is

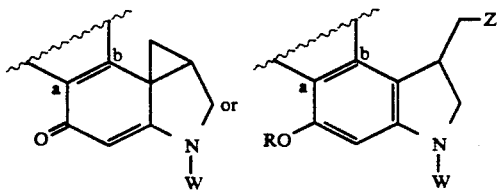

wherein Z represents Cl or Br; R represents hydrogen, CONR$^1$R$^2$ (in which R$^1$ and R$^2$ independently represent hydrogen, CONR$^1$R$^2$ (in which R$^1$ and R$^2$ independently represent hydrogen a straight-chain or branched alkyl gropu having 1 to 4 carbon atoms or phenyl),

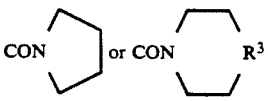

(in which R$^3$ represents CH$_2$,

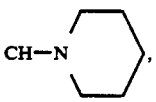

N—CH$_3$, or N—CH$_2$CONR$^1$R$^2$ in which R$^1$ and R$^2$ have the same significance as defined above); and W represents hydrogen or

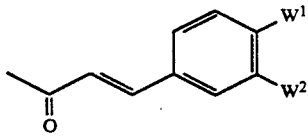

(in which W$^1$ and W$^2$ independently represent hydrogen or OR$^4$ in which R$^4$ represents a straight-chain or branched alkyl group having 1 to 4 carbon atoms or a straight-chain or branched alkenyl group having 2 to 4 carbon atoms), or a pharmaceutically acceptable salt thereof.

2. A compound according to claim 1, wherein

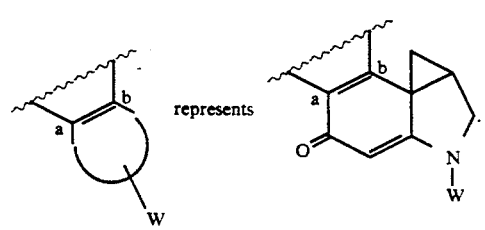

3. A compound according to claim 1, wherein

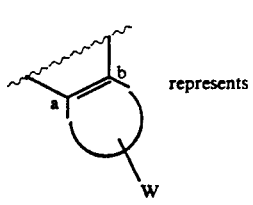 represents 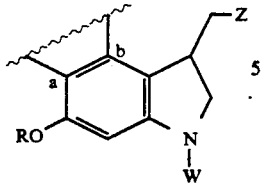

4. A compound according to claim 3, wherein X represents $CO_2CH_3$.

5. A compound according to claim 4, wherein Z represents Br.

6. A compound according to claim 5, wherein R represents

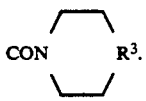

7. A compound according to claim 6, wherein $R^3$ represents $N—CH_3$.

8. A pharmaceutical composition for the treatment of tumors or infection comprising a pharmaceutical carrier and a pharmaceutically effective amount of the DC-89 derivative as defined by claim 1.

* * * * *

UNITED STATES PATENT AND TRADEMARK OFFICE
CERTIFICATE OF CORRECTION

PATENT NO. : 5,258,383

DATED : November 2, 1993

INVENTOR(S) : SATORU NAGAMURA, ET AL.

It is certified that error appears in the above-identified patent and that said Letters Patent is hereby corrected as shown below:

IN [57] ABSTRACT

Page 2, Column 2:
Line 13, "$OR^2$" should read --$OR^4$--.
Line 16, "atoms," should read --atoms),--.

COLUMN 1

Line 16, "antitumor" should read --anti-tumor--.

COLUMN 11

Line 55, "$CO_2$incubator," should read --$CO_2$-incubator,--.

COLUMN 16

Line 1, "[30 ml" should read --(30 ml--.
Line 61, "[0.12" should read --(0.12--.

COLUMN 17

"Line 20, "huH-NMR" should read --$^1$H-NMR--

COLUMN 18

Line 35, "give mg" should read --give 26 mg--.
Line 46, "(KRr)" should read --(KBr)--.

COLUMN 21

Line 45, "1.0Hz)," should read --11.0Hz),--.
Line 52, "216," should read --1216,--.

UNITED STATES PATENT AND TRADEMARK OFFICE
CERTIFICATE OF CORRECTION

PATENT NO. : 5,258,383
DATED : November 2, 1993
INVENTOR(S) : SATORU NAGAMURA, ET AL.

It is certified that error appears in the above-identified patent and that said Letters Patent is hereby corrected as shown below:

COLUMN 22

Line 21, "$CONR^1R^2$ (in which $R^1$ and $R^2$ indepen-" should be deleted.
Line 22, "dently represent hydrogen" should be deleted.
Line 23, "gropu" should read --group--.

Signed and Sealed this

Twenty-fourth Day of May, 1994

BRUCE LEHMAN

Commissioner of Patents and Trademarks